(12) United States Patent
Roger

(10) Patent No.: US 7,789,850 B2
(45) Date of Patent: Sep. 7, 2010

(54) WEIGHT CONTROLLED DIALYSIS SYSTEM WITH ACCELEROMETER

(75) Inventor: Rodolfo Roger, Clearwater, FL (US)

(73) Assignees: Baxter International Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 899 days.

(21) Appl. No.: 11/625,637

(22) Filed: Jan. 22, 2007

(65) Prior Publication Data
US 2008/0177222 A1 Jul. 24, 2008

(51) Int. Cl.
A61M 1/28 (2006.01)
(52) U.S. Cl. .............................. 604/29; 604/65; 604/67; 417/36
(58) Field of Classification Search ............... 604/7, 604/29, 65, 67, 131, 156; 417/36, 43, 44.2; 73/862.543, 152.61, 168, 863.83, 864.34
See application file for complete search history.

(56) References Cited

U.S. PATENT DOCUMENTS

| | | | |
|---|---|---|---|
| 4,560,472 | A | 12/1985 | Granzow et al. |
| 4,684,460 | A * | 8/1987 | Issautier ................... 210/90 |
| 5,141,492 | A | 8/1992 | Dadson et al. |
| 5,247,434 | A | 9/1993 | Peterson et al. |
| 5,334,139 | A | 8/1994 | Jeppsson et al. |
| 5,722,947 | A | 3/1998 | Jeppsson et al. |
| 5,762,805 | A * | 6/1998 | Truitt et al. ................. 210/645 |
| 5,776,345 | A * | 7/1998 | Truitt et al. ................. 210/645 |
| 5,782,796 | A | 7/1998 | Din et al. |
| 5,910,252 | A * | 6/1999 | Truitt et al. ................. 210/645 |
| 6,117,122 | A | 9/2000 | Din et al. |
| 6,327,895 | B1 | 12/2001 | Jeppsson et al. |
| 6,780,322 | B1 * | 8/2004 | Bissler et al. ............... 210/637 |
| 2004/0215129 | A1 | 10/2004 | Edgson et al. |
| 2007/0276328 | A1 * | 11/2007 | Childers et al. ............. 604/131 |

OTHER PUBLICATIONS

Operators Manual for Fresenius USA/Delmed 90/2 Peritoneal Dialysis System written by Fresenius USA, Inc. dated Feb. 6, 1991.
"Serena," 1 page, marketing brochure published by Gambro (undated).
"Selectra—Peritoneal Dialysis Machine for CAPD, CCPD, NPD, IPD and Manual Dialysis," 5 pages, marketing brochure written by www.medionics.com, printed on Sep. 28, 2006.
"Microstar—Volumetric Peritoneal Dialysis Cycler," 2 pages, marketing brochure written by www.medionics.com, printed on Sep. 28, 2006.
"Selectra II—Highly Efficient APD Machine for IPD, CCPD, or Tidal Dialysis," 2 pages, marketing brochure written by www.medionics.com, printed on Sep. 28, 2006.

* cited by examiner

Primary Examiner—Nicholas D Lucchesi
Assistant Examiner—Quynh-Nhu H Vu
(74) Attorney, Agent, or Firm—K&L Gates LLP

(57) ABSTRACT

A dialysis system includes: an enclosure; a dialysate pump carried by the enclosure and arranged to pump dialysate to a patient or dialyzer; at least one container connected fluidly to the dialysate pump; a load cell positioned to weigh dialysate located within the container; an accelerometer positioned and arranged to detect a force imparted on at least one of the enclosure and the container; and electronics configured to receive a first signal from the load cell and a second signal from the accelerometer and process the first and second signals so as to determine if an abnormality sensed by the load cell is a system error or a mechanical interference.

23 Claims, 7 Drawing Sheets

WEIGHT CONTROLLED DIALYSIS SYSTEM WITH ACCELEROMETER

CROSS REFERENCE TO RELATED APPLICATION

This application is related to, relies upon and incorporates by reference copending U.S. patent application Ser. No. 11/422,267 ("the '267 Application"), entitled "Dynamic Weight Balancing Of Flow In Kidney Failure Treatment Systems," filed Jun. 5, 2006, assigned to the eventual assignee of the present application.

BACKGROUND

The examples discussed below relate generally to medical fluid delivery. More particularly, the examples disclose systems, methods and apparatuses for weight controlled kidney failure treatment systems.

Due to various causes, a person's renal system can fail. Renal failure produces several physiological derangements. The balance of water, minerals and the excretion of daily metabolic load is no longer possible and toxic end products of nitrogen metabolism (urea, creatinine, uric acid, and others) can accumulate in blood and tissue.

Kidney failure and reduced kidney function have been treated with dialysis. Dialysis removes waste, toxins and excess water from the body that would otherwise have been removed by normal functioning kidneys. Dialysis treatment for replacement of kidney functions is critical to many people because the treatment is life saving.

Hemodialysis and peritoneal dialysis are two types of dialysis therapies used commonly to treat loss of kidney function. A hemodialysis ("HD") treatment utilizes the patient's blood to remove waste, toxins and excess water from the patient. The patient is connected to a hemodialysis machine and the patient's blood is pumped through the machine. Catheters are inserted into the patient's veins and arteries so that blood can flow to and from the hemodialysis machine. The blood passes through a dialyzer of the machine, which removes waste, toxins and excess water from the blood. The cleaned blood is returned to the patient. A large amount of dialysate, for example about 120 liters, is consumed to dialyze the blood during a single hemodialysis therapy. Hemodialysis treatment lasts several hours and is generally performed in a treatment center about three or four times per week.

Another form of kidney failure treatment involving blood is hemofiltration ("HF"), which is an alternative renal replacement therapy that relies on a convective transport of toxins from the patient's blood. This therapy is accomplished by adding substitution or replacement fluid to the extracorporeal circuit during treatment (typically ten to ninety liters of such fluid). That substitution fluid and the fluid accumulated by the patient in between treatments is ultrafiltered over the course of the HF treatment, providing a convective transport mechanism that is particularly beneficial in removing middle and large molecules.

Hemodiafiltration ("HDF") is another blood treatment modality that combines convective and diffusive clearances. HDF uses dialysate to flow through a dialyzer, similar to standard hemodialysis, providing diffusive clearance. In addition, substitution solution is provided directly to the extracorporeal circuit, providing convective clearance.

Peritoneal dialysis uses a dialysis solution, also called dialysate, which is infused into a patient's peritoneal cavity via a catheter. The dialysate contacts the peritoneal membrane of the peritoneal cavity. Waste, toxins and excess water pass from the patient's bloodstream, through the peritoneal membrane and into the dialysate due to diffusion and osmosis, i.e., an osmotic gradient occurs across the membrane. The spent dialysate is drained from the patient, removing waste, toxins and excess water from the patient. This cycle is repeated.

There are various types of peritoneal dialysis therapies, including continuous ambulatory peritoneal dialysis ("CAPD"), automated peritoneal dialysis ("APD"), tidal flow APD and continuous flow peritoneal dialysis ("CFPD"). CAPD is a manual dialysis treatment. The patient manually connects an implanted catheter to a drain, allowing spent dialysate fluid to drain from the peritoneal cavity. The patient then connects the catheter to a bag of fresh dialysate, infusing fresh dialysate through the catheter and into the patient. The patient disconnects the catheter from the fresh dialysate bag and allows the dialysate to dwell within the peritoneal cavity, wherein the transfer of waste, toxins and excess water takes place. After a dwell period, the patient repeats the manual dialysis procedure, for example, four times per day, each treatment lasting about an hour. Manual peritoneal dialysis requires a significant amount of time and effort from the patient, leaving ample room for improvement.

Automated peritoneal dialysis ("APD") is similar to CAPD in that the dialysis treatment includes drain, fill, and dwell cycles. APD machines, however, perform the cycles automatically, typically while the patient sleeps. APD machines free patients from having to manually perform the treatment cycles and from having to transport supplies during the day. APD machines connect fluidly to an implanted catheter, to a source or bag of fresh dialysate and to a fluid drain. APD machines pump fresh dialysate from a dialysate source, through the catheter, into the patient's peritoneal cavity, and allow the dialysate to dwell within the cavity, and allow the transfer of waste, toxins and excess water to take place. The source can be multiple sterile dialysate solution bags.

APD machines pump spent dialysate from the peritoneal cavity, through the catheter, to the drain. As with the manual process, several drain, fill and dwell cycles occur during APD. A "last fill" occurs at the end of CAPD and APD, which remains in the peritoneal cavity of the patient until the next treatment.

Both CAPD and APD are batch type systems that send spent dialysis fluid to a drain. Tidal flow systems are modified batch systems. With tidal flow, instead of removing all of the fluid from the patient over a longer period of time, a portion of the fluid is removed and replaced after smaller increments of time.

Continuous flow, or CFPD, systems clean or regenerate spent dialysate instead of discarding it. The systems pump fluid into and out of the patient, through a loop. Dialysate flows into the peritoneal cavity through one catheter lumen and out another catheter lumen. The fluid exiting the patient passes through a reconstitution device that removes waste from the dialysate, e.g., via a urea removal column that employs urease to enzymatically convert urea into ammonia. The ammonia is then removed from the dialysate by adsorption prior to reintroduction of the dialysate into the peritoneal cavity. Additional sensors are employed to monitor the removal of ammonia. CFPD systems are typically more complicated than batch systems.

People with kidney failure typically retain water and fluids between treatments. That excess fluid needs to be removed during the next treatment. It is important to know how much fluid is removed so that the patient can be returned to his or her normal weight by the end of therapy. It is also important in some instances to know accurately the rate at which ultrafiltration is taking place at a given time during therapy.

Accordingly, in each of the kidney failure treatment systems discussed above, it is important to control ultrafiltration, which is the process by which water (with electrolytes) moves across a membrane, such as a dialyzer or peritoneal membrane. For example, ultrafiltration in HD is a result of transmembrane and osmotic pressure differences between blood and dialysate across a dialyzer membrane. For a given osmotic pressure, the greater the transmembrane pressure the more rapid the ultrafiltration.

Different systems have been employed to control ultrafiltration. One system described in U.S. Pat. No. 5,247,434 ("the '434 Patent"), the entire contents of which are incorporated expressly herein by reference, controls ultrafiltration volumetrically. The patent describes a volumetrically balanced system that uses first and second chambers of substantially equal volume. Each chamber includes two compartments, one termed a "pre-dialyzer" compartment and the other a "post-dialyzer" compartment. Each opposing "pre" and "post" compartment of a chamber is separated by a flexible diaphragm. Solenoid-actuated valves control the filling and emptying of each compartment. In general, each compartment is completely filled before its contents are discharged. Also, the "pre" compartments are alternately filled and discharged and the "post" compartments are alternately filled and discharged. Filling a "pre" compartment causes a discharge of a corresponding and opposing "post" compartment, respectively. Filling a "post" compartment causes a discharge of a corresponding and opposing "pre" compartment.

Since the volumes of opposing "pre" and "post" compartments of the two chambers are equal, the system volumetrically balances the flow of dialysate to and from the dialyzer. One benefit of this volumetrically controlled system is that dialysate flow to the dialyzer can be accurately measured over a wide range of flow rates.

The volumetric system works well for HD machines placed in centers, which produce dialysate on-line. In HD, the dialysate is not infused into the patient and is therefore not considered a drug. The balancing chambers can therefore be located inside the machine and sterilized between treatments. The same balancing chambers are used over and over.

PD infuses dialysate into the patient's peritoneum. Dialysate for PD is therefore considered a drug, so that the dialysate has to meet sterility requirements for a drug. Anything that comes in contact with the dialysate must also be sterilized and discarded after use. For PD then, at least a component of the balancing chambers would have to be sterilized and disposable, making balancing chambers for PD less attractive from a cost standpoint, compared for example, to simple tubing used with peristaltic pumps.

Other fluid control systems employ scales that measure the weight of fluid delivered to and taken from the patient. Weight scales are advantageous because they eliminate the need for balancing apparatus or in-line flowmeters. One drawback of weigh scale systems is mechanical interference. The weighing system is configured to look for a particular change (increase or decrease) in weight and over time. If the weight change is too great or too little, a system error has likely occurred, such as a pump that is pumping too fast, a line kink or a leak. In such cases, the system needs to alarm the patient and take appropriate protective action.

The load cells used to control the process are also susceptible to inadvertent forces due to a person or pet bumping either the machine or one of the bags being weighed. Vibrations from a source close to the instrument could also interfere with the weight measurement. These interferences would likely cause the load cell to sense a force that is out of range or limit, causing the machine to generate an alarm even though the machine is operating properly. A need accordingly exists for weigh-type dialysis systems to eliminate or minimize errors due to mechanical interference.

SUMMARY

The examples described herein disclose dynamic weight or gravimetric balancing medical fluid flow systems and methods applicable for example to: hemodialysis ("HD"), hemofiltration ("HF"), hemodiafiltration ("HDF"), peritoneal dialysis ("PD"), including continuous ambulatory peritoneal dialysis ("CAPD"), automated peritoneal dialysis ("APD"), tidal flow APD and continuous flow peritoneal dialysis ("CFPD") modalities. The systems may also be used in any type of continuous renal replacement therapy ("CRRT"). The examples below include a diffusion membrane or filter, such as a dialyzer, e.g., for HD or HDF, a hemofilter, e.g., for HF or the patient's peritoneum, e.g., for PD. Moreover, each of the systems described herein may be used in clinical or home settings. For example, the systems may be employed in an in-center HD machine, which runs virtually continuously throughout the day. Alternatively, the systems may be used in a home PD machine, which is typically run at night while the patient is sleeping.

The examples below include a dialysate (infusate) supply, which for convenience is shown as a single bag of the fluid. Alternatively, multiple bags of dialysate supply are ganged together and used one after another. Further, alternatively, each of the systems shown below can be used with an online source, such as one or more concentrate pump configured to combine one or more concentrates with water to form dialysate on-line. On-line sources are used commonly with HD systems for example.

The present disclosure relates to dialysis systems that use load cells or scales to control the amount of fluid delivered and removed from a patient's peritoneum (PD) or a dialyzer (HD) and the amount of ultrafiltrate removed from the patient. For example, the system can employ separate fill and drain scales. The separate fill scale measures an amount of fresh fluid used for clearance from an all-bags-full weight to an all-bags-empty weight. This change in weight indicates how much fluid has been used for make clearance using either the patient's peritoneum (PD) or a dialyzer (HD).

The separate drain scale measures an amount of spent fluid increase from zero to a total spent fluid removed weight, which occurs at the end of therapy. The difference between the total spent fluid removed weight and the beginning fresh fluid weight is the weight of ultrafiltrate or excess fluid that has been removed from the patient over the course of treatment.

Alternatively, the system employs a single scale for both weigh and drain bags. This type of system in essence measures and controls ultrafiltration as the drain recovery will outweigh the weight of fresh fluid delivered to the patient.

Further alternatively, the dialysis system uses a weighing system disclosed in the '267 Application cross-referenced above. This system also uses scales or load cells but does not weigh the total fill and drain volumes. Instead, the system weighs fluid collected in a control bag, which increases in weight due to an amount of ultrafiltrate removed from the patient over time. One advantage of the '267 Application system is that the weight that the bag holds is the ultrafiltration weight essentially as opposed to the total weight of the fill and drain volumes. This system weighs a smaller volume, allowing for less error and more sensitivity than the total fill and drain systems.

The teachings of the present disclosure apply to any of the above-described types of weigh scale dialysis systems, and indeed, to any such system prone to inadvertent error due to mechanical interference.

Dialysis systems herein can fill and drain the patient (or dialyzer) using gravity or one or more fluid pumps. Different profiles may be used to deliver and remove fluid depending on a particular patient's condition and the patient's prescribed treatment. In an instrument free of interference, at any point during treatment, therefore, the rate of weight gained or lost is predictable and known. In such a system, if the rate moves instead out of a range limit placed about an expected rate, the machine is likely experiencing a system error. For example, the rate falling below a range could indicate a kinked line or leak. The rate increasing out of range could indicate that the pump controller or a pump is not operating properly. Or, a rate that is too great could indicate that a positive or negative pressure seen at the patient is out of the expected range.

The software within the instrument of the present disclosure is accordingly configured to receive signals from a load cell coupled to the weigh scale. The software in one embodiment looks for a change in the signal that is out of a range of change. For example, the software looks for a weight gain on loss of +/−Xg/hr and places a range of +/−Yg/hr about X. If the range falls outside of the X+Y or X−Y (or −X+Y or −X−Y) an error has occurred. If this happens, the machine generates an alarm and takes any other appropriate action needed, such as shutting down one or more blood, dialysate or substitution pumps, issuing visual and audible warnings, and clamping the extracorporeal circuit if applicable. In another embodiment the determination is based instead on total weight and a range about that total weight.

If during treatment the patient, another person, or a pet bumps the machine, the load cell senses this bump and resulting force spike and sends a signal to the signal processor and other software, which is indicative of the force spike. The signal can cause a false error response.

To eliminate the false response, the machine employs an accelerometer. The accelerometer is positioned with respect to the machine to detect a force applied to the machine, and in particular the weigh scale and the volume being weighed by the weigh scale. The accelerometer in one embodiment is a three-dimensional accelerometer that measures accelerations applied in three dimensions. The three-dimensional nature of the accelerometer allows nuisance trips from the machine being bumped at virtually any angle to be detected and disregarded. It also allows compensation in weight measurement error due to machine tilt.

The accelerometer is positioned on or in the machine casing so that it detects any type of jarring or bumping of the machines. The accelerometer however is positioned so that it does not detect fluid weight gain or loss. If a system error occurs, e.g., due to loss of fluid from a leak, the load cell detects such error but the accelerometer does not, in this case, the machine takes appropriate protective action. If on the other hand the load cell and accelerometer both sense a force input, the system can assume a mechanical error and prevent the unnecessary system error action.

The accelerometer sends one or more signals to signal processing and data storage software and a processing apparatus that uses software, which is configured to compare the accelerometer signal to the load cell signal. The dual load and accelerometer signals create a number of scenarios that allow the software to detect the difference between mechanical interferences (physical bumping) and actual system errors (e.g., line kinking, leaking, component failure and the like).

In one scenario, the load cell senses a change that is out of range but the accelerometer does not detect such a change. The software categorizes this scenario as a system error and causes appropriate action to be taken.

In another scenario, both the load cell and the accelerometer detect a change that is out of range, but the data produced by each signal is consistent with a particular kind of system error. For example, a scenario in which the accelerometer detects a large force imparted to the system, after which the load cell detects a continuing period of no weight change could indicate a bumping of the machine that led to a kinking or a bag being knocked off the scale. Again, the software categorizes this incident as a system failure.

In a third scenario, both the load cell and the accelerometer detect a change that is out of range, but the data produced by each signal is inconsistent with a particular kind of system error. For example, if the accelerometer and the load cell each detect an instantaneous weight change only, but the load cell thereafter detects normal operation, the software categorizes this event as mechanical interference.

As alluded to, it is also contemplated to use the accelerometer to detect a tilt or other abnormality with the dialysis machine. If the weigh scale is not positioned properly, it may not read weight correctly. The accelerometer can detect the improper position or tilt of the machine and cause the software to compensate for that improper position to read weight correctly.

It is therefore an advantage of the present disclosure to provide an improved dialysis machine or system.

It is another advantage of the present disclosure to provide an improved weigh scale type dialysis system.

It is a further advantage of the present disclosure to provide a weigh scale type dialysis system that detects and ignores nuisance mechanical interferences.

It is yet another advantage of the present disclosure to provide a weigh scale type dialysis system that prevents nuisance alarms.

It is still a further advantage of the present disclosure to provide a weigh scale dialysis system that compensates for machine tilt or improper positioning.

DETAILED DESCRIPTION

The examples described herein are applicable to any medical fluid therapy system requiring the delivery to and/or removal of fluid from a patient to be monitored and/or controlled accurately. The systems are particularly well suited for the control of kidney failure therapies, such as all forms of hemodialysis ("HD"), hemofiltration ("HF"), hemodiafiltration ("HDF"), peritoneal dialysis ("PD," including continuous ambulatory peritoneal dialysis ("CAPD")), automated peritoneal dialysis ("APD"), tidal flow APD and continuous flow peritoneal dialysis ("CFPD") modalities. The systems may also be used in any type of continuous renal replacement therapy ("CRRT").

Figure 1:
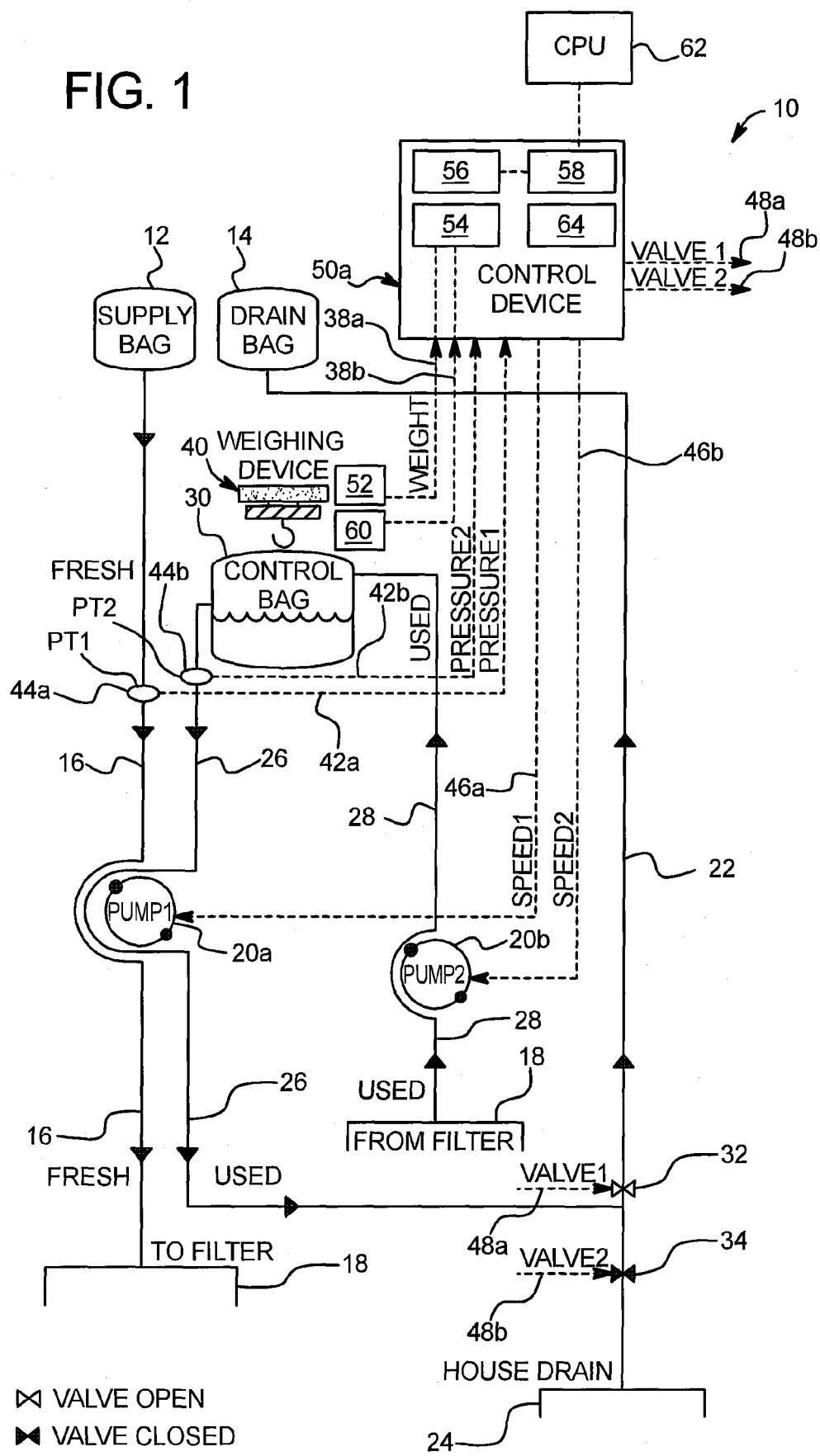
FIG. 1 is a schematic view of one type of weigh scale dialysis system employing an accelerometer according to the present disclosure.

The examples below include a diffusion membrane or filter, such as a dialyzer, e.g., for HD or HDF, a hemofilter, e.g., for HF or a peritoneum, e.g., for PD. FIG. 1 shows a to-filter and from-filter line, for example, which are used with HD. HDF includes an additional one or more fresh infusate line (not shown) leading directly to the extracorporeal circuit, either upstream or downstream (or both) from the dialyzer. The additional one or more fresh infusate lines can be teed off of the to-filter line, for example.

Instead of the to-filter line, HF runs an infusate line to the extracorporeal circuit, either upstream or downstream (or both) from the hemofilter. HF uses the from-filter line as shown in the drawings.

In PD, the type of modality dictates the tubing configuration. CAPD and APD are batch-type systems, which typically require only a single line to the patient. Dialysate in CAPD and APD is typically delivered to the patient, allowed to dwell for a period, and then pumped from the patient and discarded to a drain. Those cycles are then repeated a number of times. The to- and from-patient lines are teed together and valved appropriately, for example, so that dialysate can be delivered and removed at different times via the same line. CFPD typically uses a dual lumen catheter and thus requires the to-patient and from-patient (to-filter and from-filter) lines shown in FIG. 1.

Moreover, each of the systems described herein may be used in clinical or home settings. For example, the systems may be employed in an in-center HD machine, which runs virtually continuously throughout the day. Alternatively, the systems may be used in a home PD machine, which is typically operated at night while the patient is sleeping.

Figure 2:
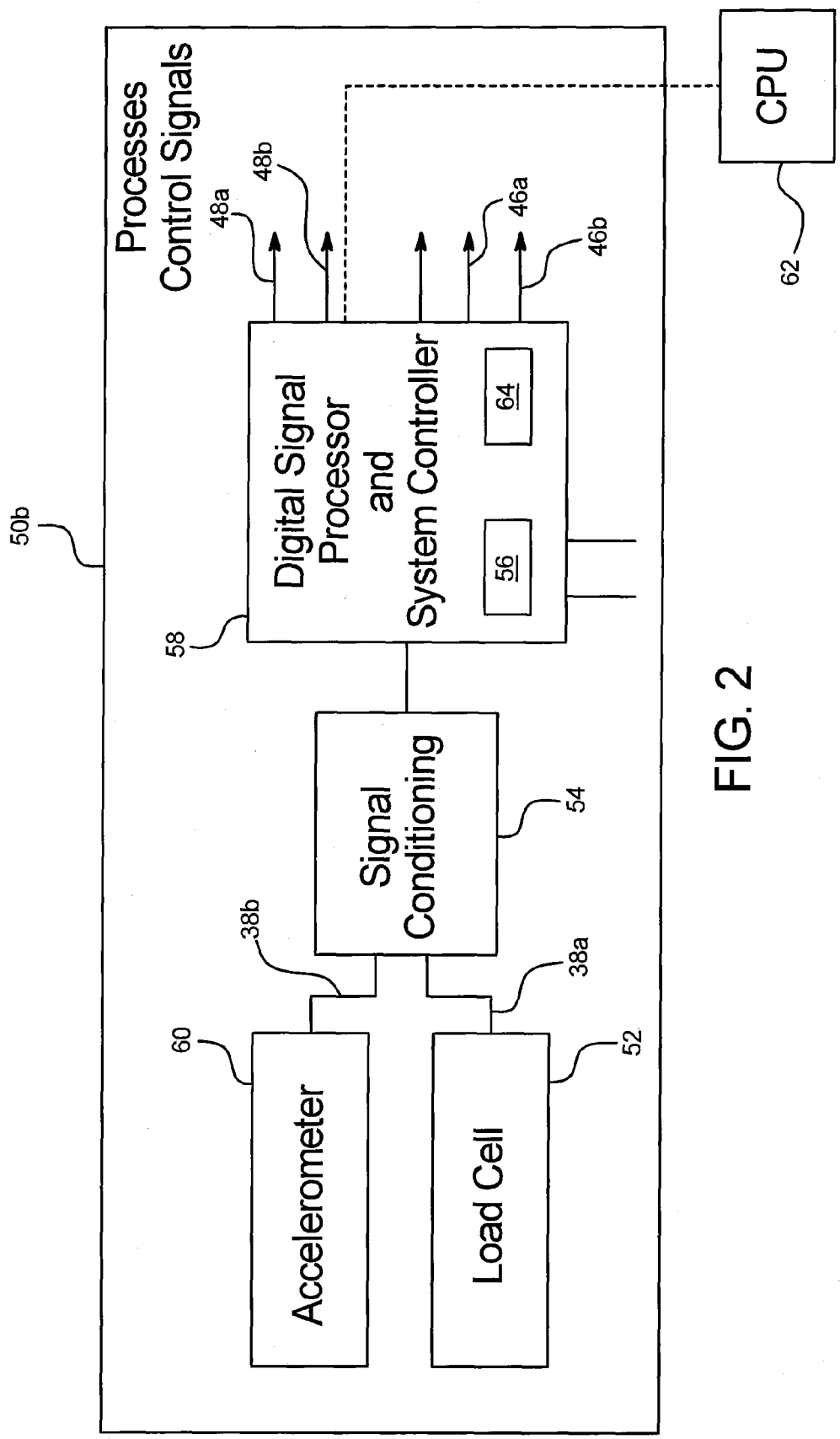
FIG. 2 is a schematic view of an alternative control scheme and signal flow process.

The examples herein include a dialysate (infusate) supply, which for convenience in FIG. 1 is shown as a single bag of the fluid. Alternatively, multiple bags of dialysate supply are ganged together and used one after another as seen in FIG. 2. In such a case, the emptied supply bags can be used later as drain or spent fluid bags. Further, alternatively, each of the systems shown herein can be used with an online dialysate source, such as one or more concentrate pumps configured to combine one or more concentrates with water to form dialysate on-line. On-line sources are used commonly with HD systems for example.

Although not illustrated, each of the systems shown and described herein can operate with an in-line or batch heater that heats the dialysate or infusate to a desired temperature. The heater can be located upstream or downstream of the fresh supply pump for example. One or more air detection and removal devices (e.g., air trap) is also provided for each of the systems in an embodiment for blood and dialysate flow. With dialysate flow, the air trap is in many instances located at or near the heater to capture air egressioning from the solution due to heating.

The flow schematics shown in FIG. 1 show the dialysate or infusate portion of the kidney failure therapy device. HD, HF and HDF machines also include blood pumping systems. HD, HF and HDF also include dialysate proportioning systems, mentioned above, which are also known and need not be described here. The '434 Patent, incorporated herein by reference, describes one suitable proportioning system.

The dynamic weighing systems described herein can be used for a number of purposes. One purpose is to know how much dialysate has been used for clearance via either a dialyzer or the patient's peritoneum. Another purpose is to control ultrafiltration volume. The systems provide an accurate and relatively non-complex way of controlling and knowing how much ultrafiltrate has been removed from the patient. The systems ensure that the necessary amount of fluid is removed from the patient by the end of treatment.

Additionally, the systems can be used to control ultrafiltration ("UF") rate. The '434 patent, incorporated herein by reference, describes UF profiling, which enables the rate at which fluid is removed from the patient to vary desirably over the course of treatment. Because the weighing systems are dynamic, they allow information to be determined on a real time basis. For example, the systems can determine that one hundred milliliters ("ml's") of fluid have been removed from the patient over the past minute, yielding a UF rate of 100 ml/min. That actual rate can then be compared to a desired rate set according to a prescribed UF profile, so that the pumps can be adjusted if needed to make the actual rate equal the desired rate.

The systems described herein are also provided in an enclosure, shown, e.g., in FIG. 2. The enclosures vary depending on the type of treatment, whether the treatment is in-center or a home treatment, and whether the dialysate/infusate supply is a batch-type (e.g., bagged) or in-line. The in-center, in-line enclosures tend to be bigger and more robust due to the additional dialysate producing equipment and the frequency the use of such machines. Home therapy enclosures are desirably smaller and built so that the machines can be moved about one's home or for travel.

Referring now specifically to FIG. 1, one example of a dynamic weight or gravimetric balancing system having load cell and accelerometer feedback is illustrated by the system 10. In FIG. 1, valves that are currently open are shown unbolded or uncolored, while valves that are currently closed are shown bolded or colored. System 10 includes a dialysate or replacement fluid supply 12, which can be any of the types described above including multiple supply bags. As used herein, the term "dialysate" is meant to cover any of the batch or online fluids prepared in any of the treatments discussed above, including dialysate for HD and HDF. The term also encompasses any dialysate made for any batch or continuous type of PD system (dialysate for PD includes glucose in a high concentration). Further, the term dialysate covers replacement fluid used in HF and HDF.

System 10 also includes a drain bag 14, which can be a single drain bag, a plurality of drain bags, or a large drain container. System 10 also includes a house drain 24, which can be a toilet or any type of drain installed in a hospital, home or clinic. A fresh dialysate line 16 is connected fluidly to dialysate supply 12 and the inlet of filter 18. Filter or diffusion membrane 18 can be any of the types discussed above. Dialysate supply line 16 is also coupled operably to a first pump 20a, which in one embodiment is a peristaltic pump.

A drain line 22 is connected fluidly between drain bag 14 and/or house drain 24. A first spent dialysate line 26 is connected fluidly to a control container 30 and drain line 22. First spent dialysate line 26 is also coupled operably (along with fresh supply line 16) to first peristaltic pump 20a. A second spent dialysate line 28 is connected fluidly to the outlet of filter or diffusion membrane 18 and control bag 30. Second spent dialysate line 22 is coupled operably to peristaltic pump 20b. First and second valves 32 and 34 as illustrated are configured to selectably occlude drain line 22 at positions located on either side of the fluid connection between first spent dialysate line 26 and drain line 22.

As illustrated, peristaltic pump 20a has a common head that drives fresh dialysate from supply 12, through fresh supply line 16 to the input of filter 18, while at the same time pulling the spent dialysate from control bag 30, through the first spent dialysate line 26, to drain line 22, and thereafter to either drain bag 14 or house drain 24.

Figure 5:
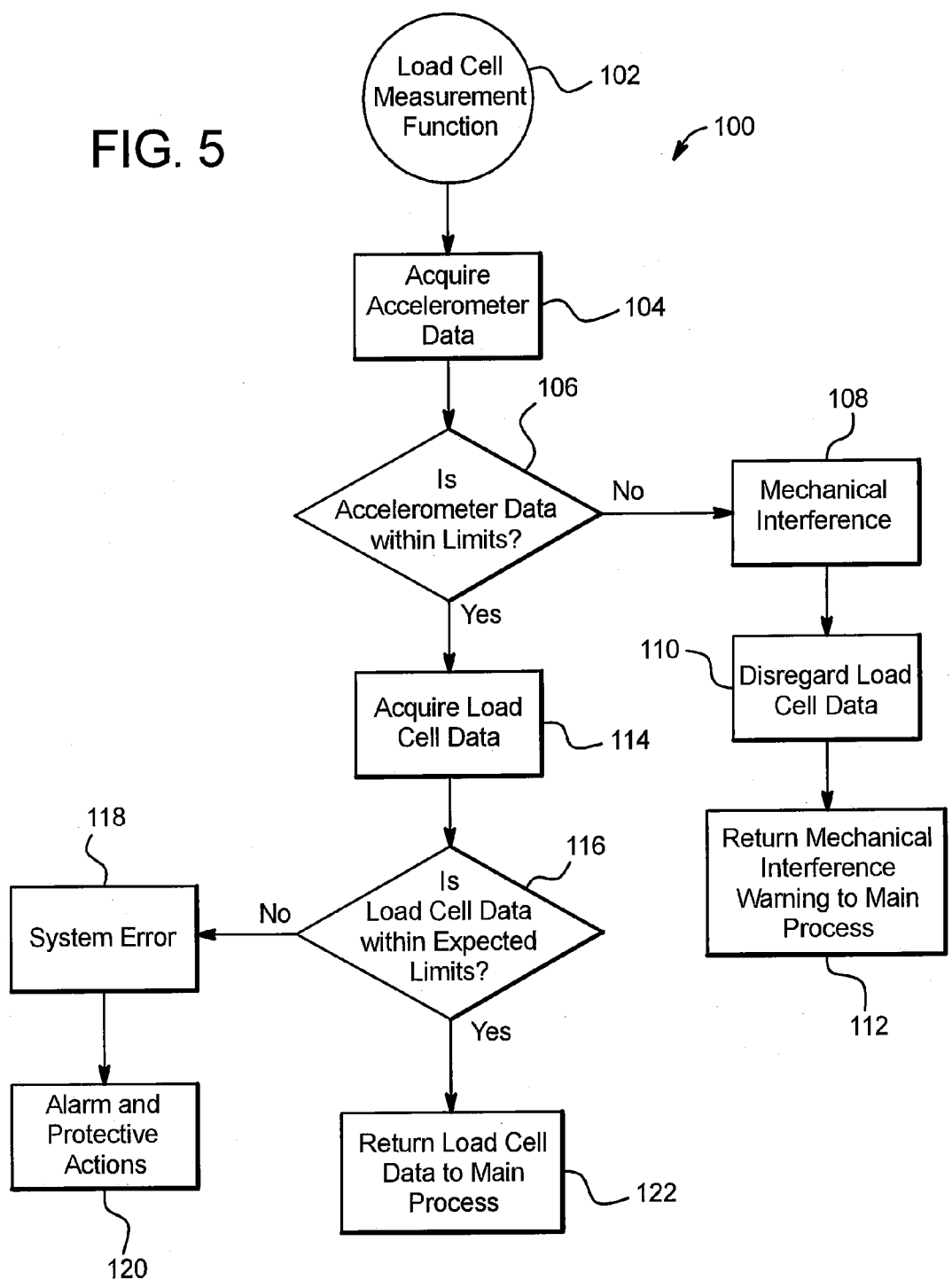
FIG. 5 is a schematic view of one embodiment of an algorithm embodied in the dialysis systems of the present disclosure.
Figure 6:
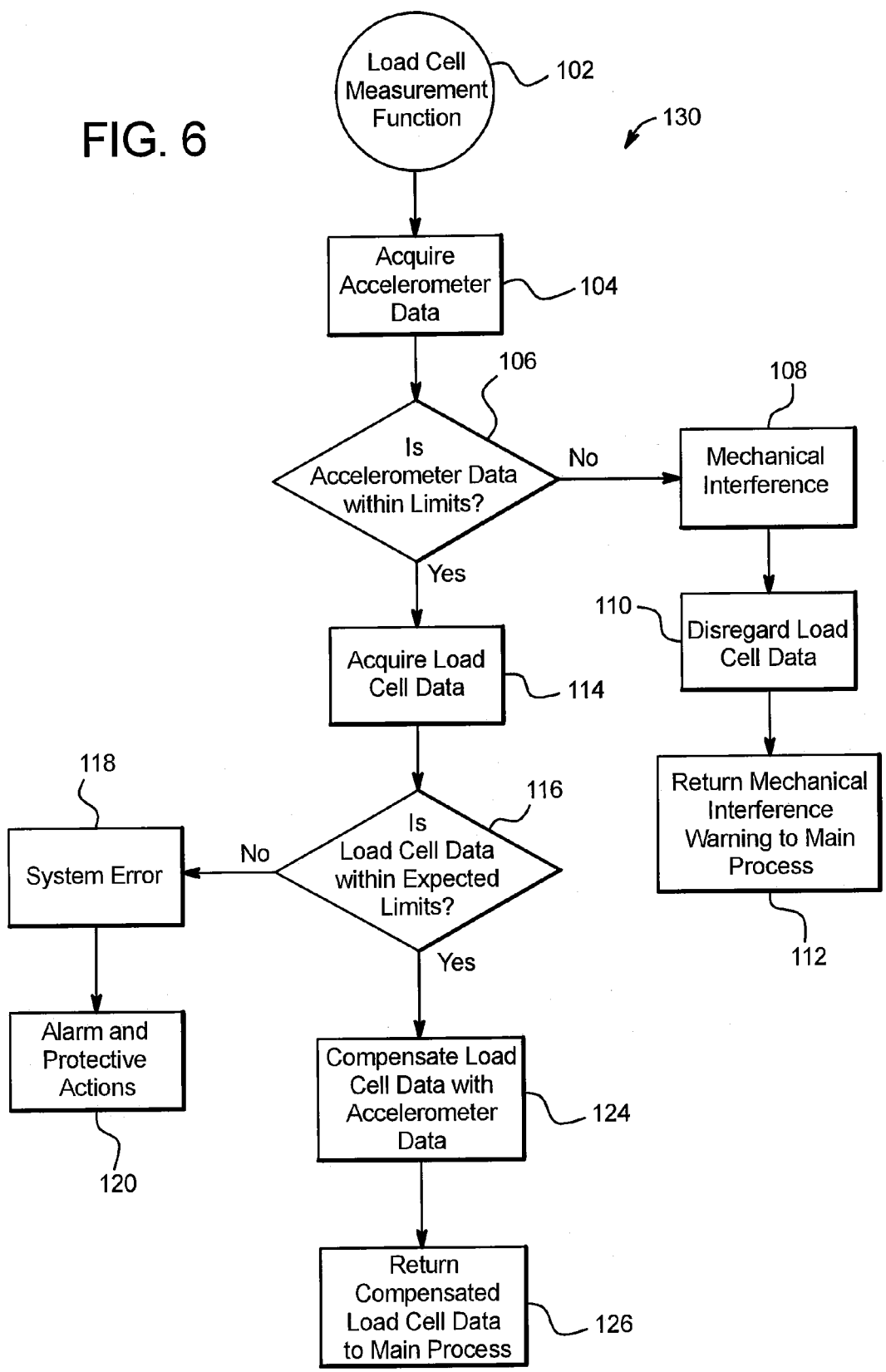
FIG. 6 is a schematic view of another embodiment of a algorithm embodied in the dialysis systems of the present disclosure.
Figure 7:
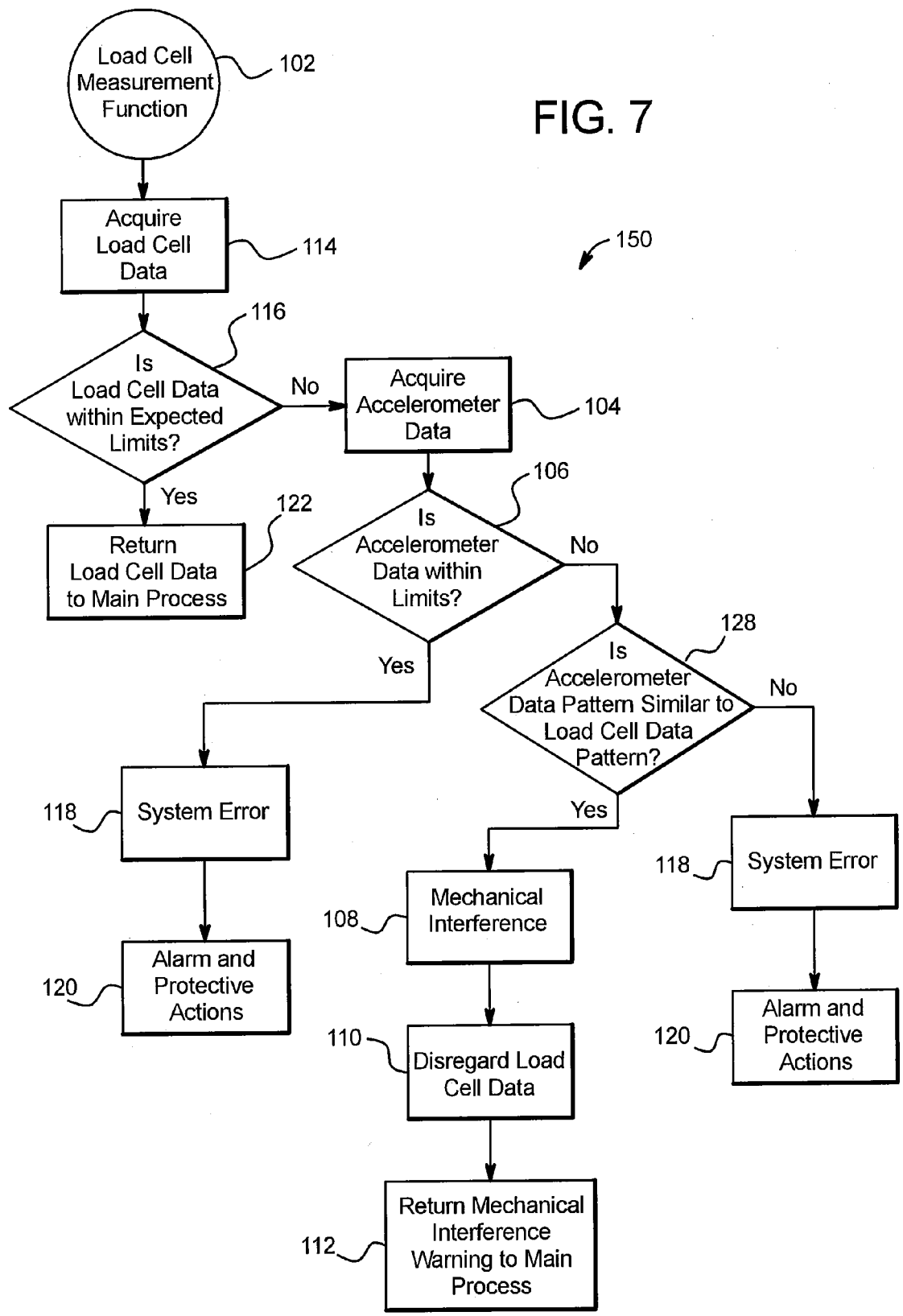
FIG. 7 is a schematic view of a further embodiment of an algorithm embodied in the dialysis systems of the present disclosure.

Control bag 30 is coupled operably to a weighing device or scale 40. Weighing device 40, which can include a pan, hanger, control container, etc., is also connected operably to a load cell 52 and accelerometer 60. Any of the embodiments shown below in connection with FIGS. 5 to 7 is applicable to any of the systems described herein, including system 10.

Load cell 52 and accelerometer 60 send an electronic signals 38a and 38b, respectively, such as a zero-to-five VDC or four-to-twenty mA analog signals or alternatively pulse-width-modulated digital signals as discussed in more detail below to a control device 50a. Control device 50a can be any suitable type of logic implementer, such as one containing any one or more of signal conditioning 54, a digital signal processor ("DSP") 58, a random access memory ("RAM") 56, a read-only memory ("ROM") 64, or an application specific integrated circuit ("ASIC", not illustrated). Signal conditioning 54, for example, includes an analog to digital converter, an amplifier and signal integration, etc.

Load cell 52 is positioned to sense the weight of control bag 30. Accelerometer 60 on the other hand is positioned on or in the casing of the system 10, such that it does not sense a change in the weight of control bag 30. In this manner, if both load cell 52 and accelerometer are tripped, a mechanical interference has likely occurred. If only load cell 52 detects an abnormal change, a system error, e.g., a leak, has likely occurred. Various algorithms for coordinating the output of load cell 52 and accelerometer 60 are discussed below in connection with FIGS. 5 to 7.

In an embodiment, control device 50a is a subcontroller and is provided on a delegate printed circuit board ("PCB"), which may communicate with one or more supervisory, master control or motherboard central processing unit ("CPU") 62, located separately from control device 50a, which in turn communicates with other delegate controllers within system 10. For example, control device 50a can control certain related functions, such as UF control, dialysate proportioning, dialysate pressure control, dialysate temperature control, and other related dialysate parameters. The use of subcontrollers in combination with one or more motherboards is discussed in the '434 Patent, incorporated herein by reference.

Besides signals 38a and 38b, control device 50a receives and generates additional signals, which may be of any suitable type including those listed above for signals 38a and 38b. Any of the signals generated and/or received by control device 50a may be analog or digital. For example, control device 50a also receives pressure signals 42a and 42b from pressure transducers 44a and 44b, respectively. Control device 50a further generates and sends signals 46a and 46b to pumps 20a and 20b. In an embodiment, signals 46a and 46b are variable current signals that control the speed of pumps 20a and 20b. Signals 46a and 46b are alternatively pulsed voltage or transistor-transistor logic ("TTL") type signals that are sent to a local controller at pumps 20a and 20b. The local pump controllers convert the digitized signals into motor currents that control the speed of pumps 20a and 20b.

Control device 50a also sends signals 48a and 48b to valves 32 and 34. Valves 32 and 34 in an embodiment are normally open or normally closed solenoid valves. Signals 48a and 48b electronically and automatically control whether any particular valve is open or closed at any particular time. Control device 50a in an embodiment maintains software that sequences the valves, such as valves 32 and 34 at appropriate times. Control device 50a also maintains software that compares the value at any given time for signals 38a and 38b from weighing device 40 with a preset or desired value or range, which determines whether enough fluid is maintained within control bag 30 or whether UF rate is proper, and thus whether to speed up or slow down one or both of pumps 20a and 20b. The use of signals 38a and 38b is discussed in detail below.

Alternatively, CPU 62 commands one or more different delegate controller to do one or more of input pressure signals 42a and 42b, output pump signals 46a and 46b and valve signals 48a and 48b. In this control scheme controller 50a operates at least primarily as a load cell and accelerometer controller.

As noted above, system 10 includes an accelerometer 60. Accelerometer 60 measures acceleration, i.e., inherently measures its own motion (locomotion). Accelerometer 60 in an embodiment is located on a separate PCB with load cell 52. Wires or leads are run from accelerometer 60 to the PCB of control device 50a. Alternatively, accelerometer 60 is located on the PCB of control device 50a. Accelerometer 60 can be housed in the enclosure of the dialysis machine. Importantly, accelerometer 60 is positioned to be able to sense forces applied to control bag 30, which may cause nuisance alarms from load cell 52, and so that the accelerometer can compensate for an improper positioning or tilt of device 30.

Accelerometer 60 in one embodiment uses Micro Electro Mechanical System ("MEMS") technology, usually including a suspended cantilver beam or proof mass (also known as seismic mass) in combination with deflection sensing and circuitry. Single axis, dual axis, and three axis models are available. These devices are used in cars, for example, for air bag deployment upon sensing a high rate of deceleration.

Accelerometer 60 in another embodiment uses a piezoelectric effect. Here, the accelerometer contains microscopic crystal structures. Mechanical interference of system 10, e.g., bumping the system, stresses the crystals causing a proportional voltage to be generated. Accelerometer 60 alternatively senses changes in capacitance. Here, the accelerometer places two structures next to each other causing a certain capacitance between the structures. When a force moves one of the structures the capacitance between the structures changes. Circuitry with the accelerometer or on the PCB of device 50a converts capacitance to voltage. In further alternative embodiments, accelerometer 60 can use a piezoresistive effect, hot air bubbles, or light instead.

Signal 38b from accelerometer 60 can be an analog or digital signal. For example, an analog accelerometer can output a continuous voltage that is proportional to acceleration, e.g., 2.5 VDC for 0 g, 2.6 VDC for 0.5 g, 2.7 VDC for 1 g, etc. Control device 50a in one embodiment is configured to accept analog inputs. System 10 in an alternative embodiment uses signal conditioning, such as one or more analog to digital converter 54, which converts analog load cell and accelerometer signals into a digital form for processing at control device 50a. For proper A/D conversion, accelerometer 60 should have a relatively low output impedance, e.g., from under 10 kΩ to about 35 kΩ.

In a further alternative embodiment, a digital accelerometer 60 is provided, which uses pulse width modulation ("PWM") to output a square wave of a certain frequency, for which the amount of time the voltage is high is proportional to the amount of acceleration applied to system 10. Here, control device 50*a* is configured to accept a digital accelerometer signal 38*b*.

Given that system 10 can be bumped from virtually any angle, a three-axis accelerometer may be preferred, however, it is also contemplated to use a two-axis accelerometer. Further alternatively, two two-axis accelerometers are provided and positioned at right angles to each other. It is believed that a ±2 g accelerometer should provide enough headroom for the vast majority of forces that will be applied to system 10.

Accelerometer 60 serves multiple purposes for system 10. Accelerometer 60 measures an amount of static acceleration due to gravity to determine an angle (if any) at which the dialysis machine of system 10 is tilted with respect to the earth. For example, a table upon which system 10 is set may be tilted. Weigh scale 40 may only therefore be reading the axial vector component of the true weight of fluid inside control bag 30. Accelerometer 60 detects the angle at which control bag 30 is tilted and allows control device 50*a* to compensate for the tilt.

Accelerometer 60 also measures an amount of dynamic acceleration due for example to a mechanical bumping of the machine or control bag 30 of system 10. Accelerometer 60 using any necessary signal conditioning 54 sends data 38*b* to buffering RAM 56, which stores that data and software that operates with the data. Similarly, load cell 52 measures the strain applied by the weight of fluid within control bag 30 and sends a signal 38*a* using any necessary conditioning 54 to RAM 56. Digital signal processor ("DSP") 58 processes the data using the software to determine if data received from load cell 52 is correct weight data, system error or mechanical error.

In the embodiment illustrated in FIG. 1, signal conditioning 54, RAM 56, ROM 64 and DSP 58 are located on the PCB of control device 50*a* in one embodiment. DSP 58 communicates with the central processing unit ("CPU") 62 of the machine of system 10 and informs CPU 62 whether system or mechanical error has occurred. CPU 62 then causes the machine of system 10 to take an alternative action. Various algorithms for control device 50*a* of system 10 are discussed below. RAM, ROM and DSP may be integrated in only one integrated circuit.

An alternative embodiment for the control device of the present disclosure is illustrated by control device 50*b*. In an embodiment, control device 50*b* is PCB based. Here, data streams 38*a* and 38*b* from load cell 52 and accelerometer 60, respectively, are fed to signal conditioning 54, which operates as described above to condition the data streams. Signal conditioning outputs to DSP 58. Here, DSP 58 includes RAM 56 and ROM 64. DSP 58 in an embodiment also receives pressure signals 42*a* and 42*b*. DSP 58 may also relay information to CPU 62.

Alternatively, CPU 62 commands one or more different delegate controller to do one or more of input pressure signals 42*a* and 42*b*, output pump signals 46*a* and 46*b* and valve signals 48*a* and 48*b*, leaving DSP 58 and controller 50*b* to operate at least primarily as a load cell and accelerometer controller. Controller 50*b* can perform any of the functions described above for controller 50*a*.

Figure 3:
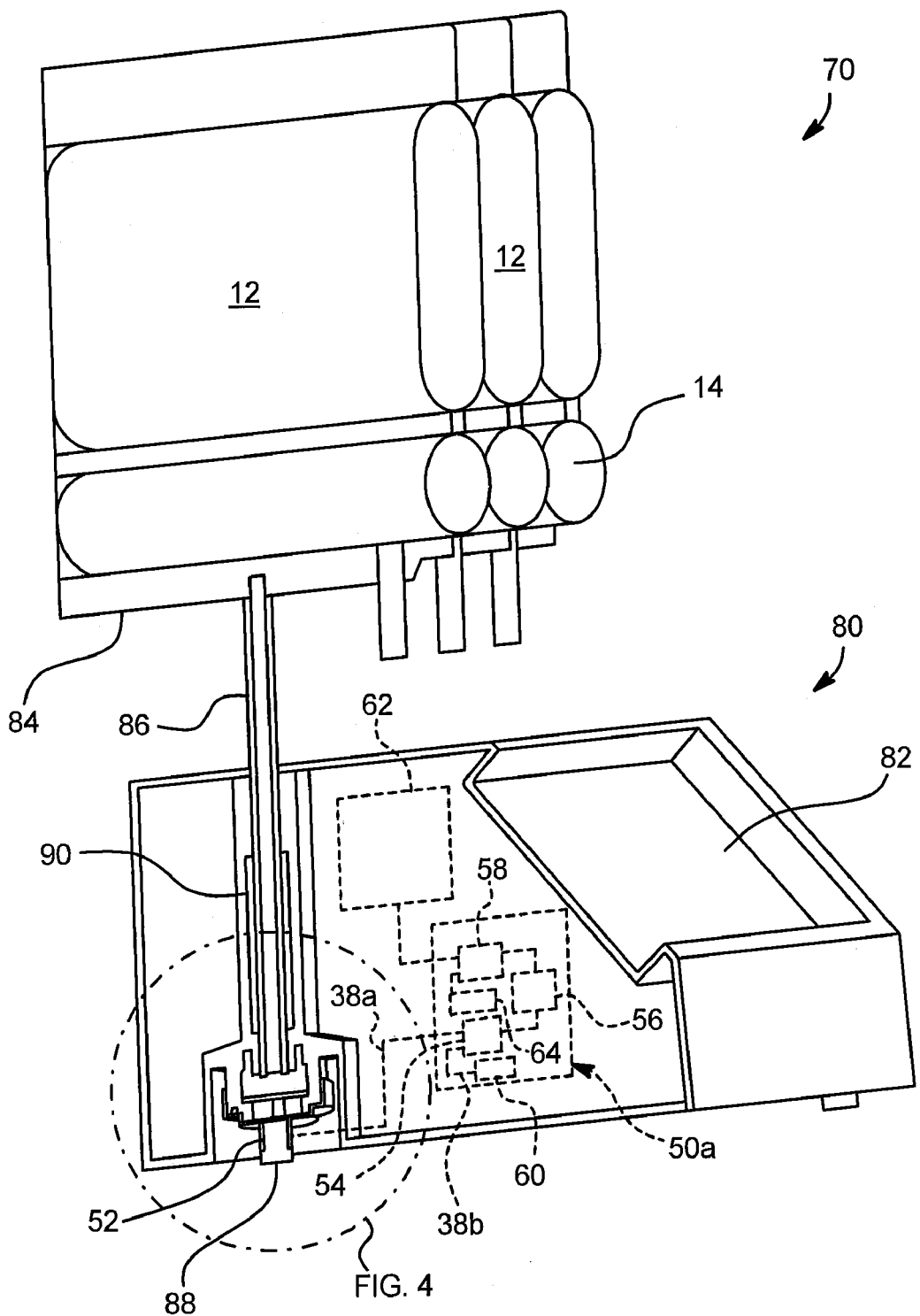
FIGS. 3 and 4 are perspective views of another type of weigh scale dialysis machine showing one possible positioning for the cooperating load cell and accelerometer according to the present disclosure.
Figure 4:
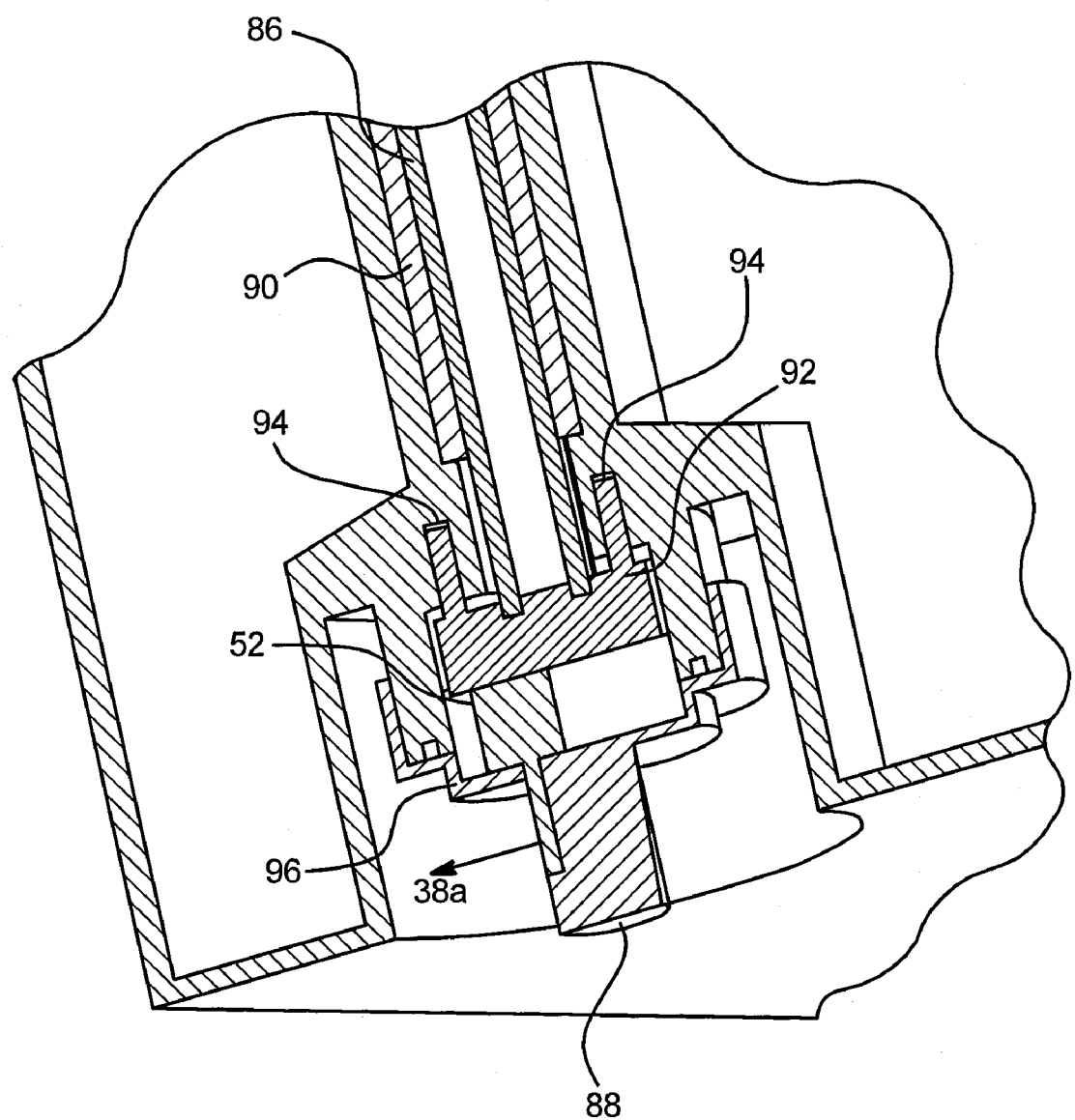

Referring now to FIGS. 3 and 4, an alternative weight controlled system 70 is illustrated. System 70 controls the amount of dialysate exchanged and ultrafiltrate removed by measuring the weight of fluid within supply bags 12 and drain bag 14. In the illustrated embodiment, a single scale is employed that accounts for both fresh fluid lost and spent fluid gained. Here, because a net volume of fluid is removed or ultrafiltered from the patient, system 70 expects to see an increase in weight over time.

Alternatively (not illustrated), a first scale for the fresh bags 12 and a second scale for the drain bag 14 is used. System 70 in that case sums two weight signals to determine the amount of ultrafiltrate accumulated for any give point in time. Although system 70 of FIGS. 3 and 4 uses a single scale, the dual scale approach may be used instead. In either case, one disadvantage of system 70 compared to system 10 is that system 70 requires the patient to have each supply and drain bag positioned properly onto stand 84.

In FIG. 3, a blood treatment machine 80 is illustrated. In the illustrated embodiment, blood machine 80 accepts one or more cassette (e.g., blood cassette or dialysate cassette) at cassette loading portion 82, which is on a front, angled part of machine 80. Bags 12 and 14 are loaded onto stand 84. Stand 84 is coupled to a shaft 86.

FIG. 4 shows an enlarged view of the cutaway in FIG. 3 and that shaft 86, stand 84 and bags 12 and 14 are supported by a foot 88 that rests on a table or wherever machine 80 is placed for treatment. Shaft 86 is movable linearly within a linear bearing 90. A cap 92 having a plurality of anti-rotation pins 94 is fitted to the end of shaft 86 and moves with the shaft. Pins 94 reside within mating slots or grooves defined in the housing of machine 80. Pins 94 and the mating slots or grooves enable shaft 86 to move linearly but not rotationally with respect to machine 80.

A load cell 52, which may be any of the types discussed herein, is provided for example at a base 96, which is coupled to supporting foot 88. Load cell 52 measures the strain applied by the weight of fluid within bags 12 and 14 and sends a signal 38*a* using any necessary conditioning 54 to RAM 56, which also stores software (e.g., for one of the algorithms shown below) to be used in conjunction with the buffered data from load cell 52.

Accelerometer 60 in the illustrated embodiment is provided on the PCB of control device 50*b*. Accelerometer 60 is positioned to measure any mechanical force, e.g., bumping, applied to machine 80, e.g., to bags 12 and 14, and sends a signal using any necessary conditioning 54 to RAM 56. DSP 58 processes any load cell 52 and accelerometer 60 data using the software and communicates with CPU 62 as described herein to determine the corresponding weight in bags 12 and 14, a system error condition or mechanical error. In the illustrated embodiment, accelerometer 60 is positioned not to detect a weight gain or loss of fluid from bags 12 and 14. In this manner, if both load cell 52 and accelerometer 60 are tripped, a mechanical interference has likely occurred. If only load cell 52 detects an abnormal change, a system error, e.g., a leak, has likely occurred. Various algorithms for coordinating the output of load cell 52 and accelerometer 60 are discussed below in connection with FIGS. 5 to 7.

Referring now to FIGS. 5 to 7, various embodiments for algorithms or logic flow charts embodied in the software described above are illustrated. These algorithms may be used with either system 10 or system 70 discussed above. The algorithms vary in complexity and functionality. The algorithms of the flow charts of FIGS. 5 and 7 pertain to the dynamic data of accelerometer 60. The algorithm or flow chart of FIG. 6 also incorporates static tilt data.

FIG. 5 shows logic flow diagram 100. At step 102, a load cell measurement function is initiated, for example, after it is confirmed that any supply bag 12, drain bag 14 or control bag has been positioned properly with respect to load cell 52 and accelerometer 60. The load cell 52 and accelerometer 60 will detect the connection and loading of bags 12 and 14, which is not necessary. The system also likely waits for pumping to begin before initiating weighing and mechanical interference detection. At step 104, system 10, 70 acquires accelerometer data, e.g., according to a bandwidth rate of accelerometer 60.

At step 106, logic flow diagram 100 determines whether data from accelerometer 60 is within limits. This can be done in a number of ways. In one way, a change in accelerometer signals from static to dynamic is compared to an acceptable change to determine if the change is within limits. Accelerometer 60 for example generates a static force F1 in the negative z direction. If a force F2 is generated in the negative z direction, logic flow diagram 100 subtracts F1 from F2 to determine if the ΔF is outside acceptable limits. Likewise, accelerometer 60 may generate a static force of zero in the horizontal x-y plane. If a force F is generated in the x-y plane, logic flow diagram 100 subtracts zero from F to determine if the ΔF (here, =F) is outside acceptable limits. Alternatively, diagram 100 looks only at the dynamic force (F2 or F in examples above) to determine if the dynamic force is over a limit.

In either case, multiple digital signals can be integrated or a continuous analog signal can be monitored over a period of time to ensure that accelerometer 60 is operating properly. The classification determination made in connection with step 106 can also look at duration of the dynamic signal. A bumping of the machine likely produces a large force spike over a relatively short period of time. Thus shorter, non-sustained, force pulses can also point towards mechanical interference, while a sustained force could be a sustained mechanical interference, e.g., something that has fallen onto the machine or be system error.

If under any analysis above the accelerometer data is outside of limits as seen at step 108, DSP 58 determines that a mechanical interference has occurred and sends a signal to CPU 62 to disregard any error signals from load cell 52, as seen in connection with step 110. Afterwards, the mechanical interference warning function is returned or reset to normal operation as seen at step 112.

On the other hand, if under any analysis above the accelerometer data is within limits as seen at step 108, load cell data is acquired as seen at step 114. It should be appreciated that load cell 52 is constantly monitoring systems 10, 70, e.g., according to a bandwidth associated with load cell 52. Thus the acquisition of load cell data could be initiated earlier at step 104 without changing logic flow diagram 100. That is, load cell data does not have to be taken at the point in the sequence of step 114. It could happen however that while load cell data is being generated continuously, logic flow diagram 100 is configured to go and acquire the current reading at step 114.

In any event, logic flow diagram 100 determines whether data from load cell 52 is within limits as seen at step 116. In one implementation, a change in load cell signals over a set period of time is compared to an acceptable change for that period of time to determine if the change is within limits. Systems 10 and 70 illustrated above both measure an amount of ultrafiltration ("UF") removed from the patient. Thus, DSP 58 would expect to see a gradual increase in weight over time. UF profiles may be employed in which UF rate is expected to change over time. Regardless, if load cell 52 senses a UF rate that is out of range, e.g., + or −X % from an instantaneous demanded rate, the load cell data is deemed to be out of range.

A similar but more complex analysis is applied to a dual load cell system, which measures fill and drain independently. Here, fill weight is expected to drop, drain weight is expected to increase, and the sum of the two signals, which yields UF rate, is also expected to increase. In an embodiment, the within limits load cell determination is made with respect to the fill and drain weights only, i.e., not independently for UF rate. An error in either also indicates an erroneous UF rate. The individual rates are monitored as just described for the monitoring of UF measuring scales.

If the load cell data is outside of limits as seen at step 118, DSP 58 determines that a system error has occurred and sends a signal to CPU 62 to cause an audio, visual or audiovisual alarm to be made and to cause any other needed step to occur, e.g., shutting down one or more pump, occlude one or more valve or tube, etc., as seen in step 120. System errors include a kinked line, a leak, a faulty component or sensor, etc.

If on the other hand, the load cell data is within limits as seen at step 122, no alarm condition exists and the load cell warning function is returned or reset to normal operation as seen at step 122. As seen in connection with logic flow diagram 100, the software here in effect filters out mechanical interference before allowing a load cell out of limits determination to be made.

Referring now to FIG. 6, an alternative logic flow diagram 130 is illustrated. Logic flow diagram 130 is similar to logic flow diagram 100. Like steps are accordingly numbered the same.

Logic flow diagram 130 adds step 124, which compensates load cell data with accelerometer data. Step 124 integrates the static readings from accelerometer 60 after it has been determined that no dynamic event has occurred and that the system is operating normally albeit potentially with a vector offset or tilt. Here, if three dimensional accelerometer 60 senses a force in the horizontal x-y plane, system 10, 70 knows that whatever bag is being weighed is resting on a member having a slight tilt and that the −z or gravity reading is likely less than actual. By comparing the composite x-y force component with the −z or gravity component, logic flow diagram 130 at step 124 can determine the degree of the tilt and compensate for it, providing an overall more accurate system. At step 126, the load cell warning function is returned or reset to normal operation with compensated load cell data.

Referring now to FIG. 7, a further alternative logic flow diagram 150 is illustrated. Logic flow diagram 150 is similar to logic flow diagrams 100 and 130 in many steps. Like steps are accordingly numbered the same.

One difference with logic flow diagram 150 is that the load cell data acquisition step 114 and load cell within limits determination 116 are shown as being performed before the accelerometer acquisition step 104 and accelerometer and limits determination 106. The step sequence is interchangeable and the independent acquisitions 114/104 and determinations 116/106 can also be made simultaneously. Here, if load cell data is within limits, normal operation is determined at step 122 regardless of whether accelerometer data is within limits at step 106. Also, if load cell data is out of limits at step 116 and accelerometer data is within limits at step 106, a system error has occurred as seen at step 118.

The primary difference in flow diagram 150 occurs when both load cell 52 and accelerometer 60 data are out of limits. In such a case, flow diagram 150 at step 128 determines whether the accelerometer data pattern is similar to the load cell data pattern. The load cell and accelerometer signals under mechanical interference type out of limits operation have a similar pattern of amplitude versus time. That is, both accelerometer 60 and load cell 52 will register a sudden change during mechanical interference. In this manner, if the accelerometer data pattern is similar to the load cell data pattern, as seen at step 128, DSP 58 determines that a mechanical interference has occurred and sends a signal to CPU 62 to disregard any error signals from load cell 52, as seen in connection with step 110. Afterwards, the mechanical interference warning function is returned or reset to normal operation as seen at step 112.

If the data pattern of accelerometer 60 shows no excitation, while load cell 52 shows a sudden change, e.g., data are dissimilar, as seen at step 118, DSP determines that a system error has occurred and sends a signal to CPU 62 to cause an audio, visual or audiovisual alarm to be made and to cause any other needed step to occur, e.g., shutting down one or more pump, occlude one or more valve or tube, etc., as seen in step 120. Because accelerometer 60 is not positioned to detect the weight of liquid inside the bags, not sensing directly under the shaft of the bag organizer) fluid can be added or removed from the bags without the accelerometer detecting such addition or loss. For example, 30 mL at a time when such gain or loss is not expected or pre-programmed, could create a system error and not trip accelerometer 60.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A dialysis system comprising:
   an enclosure;
   a dialysate pump carried by the enclosure and arranged to pump dialysate to a patient or dialyzer;
   at least one container connected fluidly to the dialysate pump;
   a load cell positioned to weigh dialysate located within the at least one container;
   an accelerometer positioned and arranged to detect a force imparted on at least one of the enclosure and the container; and
   electronics configured to receive a first signal from the load cell and a second signal from the accelerometer and process the first and second signals so as to determine if an abnormality sensed by the load cell is a system error or a mechanical interference,
   wherein the electronics are further configured such that if the second signal yields an abnormal accelerometer condition, the load cell abnormality is categorized as a mechanical interference.

2. The dialysis system of claim 1, wherein the pump in a supply pump, and which includes at least one drain pump connected fluidly to the container.

3. The dialysis system of claim 1, wherein the container includes at least one of a supply container, a drain container and an ultrafiltrate container.

4. The dialysis system of claim 1, wherein at least one of the load cell and the accelerometer is coupled operably to a pan or hook, the container loaded on the pan or hook.

5. The dialysis system of claim 1, wherein the mechanical interference includes a inadvertent force applied to the machine.

6. The dialysis system of claim 1, wherein the system error is at least one of a kinked line, a leak, a component failure and a sensor failure.

7. The dialysis system of claim 1, wherein the electronics are configured to process a plurality of the first signals to determine if a change in the first signals is out of a range of acceptable change.

8. The dialysis system of claim 1, wherein the electronics are configured to process a plurality of the second signals to determine if a change in the second signals is out of a range of acceptable change.

9. The dialysis system of claim 1, wherein the electronics are configured such that if the second signal yields a normal accelerometer condition, the load cell abnormality is categorized as a system error.

10. The dialysis system of claim 1, wherein the electronics are configured such that if the second signal yields an abnormal accelerometer condition, and the load cell abnormality and the abnormal accelerometer condition are consistent with a system failure, the load cell abnormality is categorized as a system error.

11. The dialysis system of claim 1, wherein the electronics are configured such that if the second signal yields an abnormal accelerometer condition, and the load cell abnormality and the abnormal accelerometer condition are inconsistent with any type of system error, the load cell abnormality is categorized as a mechanical interference.

12. The dialysis system of claim 1, wherein the electronics include at least one of: a processor, a memory and a signal conditioner.

13. The dialysis system of claim 1, wherein the accelerometer is configured and positioned such that it does not weigh dialysate located within the at least one container.

14. A dialysis system comprising:
    an enclosure;
    a dialysate pump carried by the enclosure and arranged to pump dialysate to a patient or dialyzer;
    at least one container connected fluidly to the dialysate pump;
    a load cell positioned to weigh dialysate located within the at least one container;
    an accelerometer positioned and arranged to detect a force imparted on at least one of the enclosure and the container; and
    electronics configured to receive load cell data from the load cell and accelerometer data from the accelerometer and process the load cell and accelerometer data to determine if (i) the dialysis system is operating properly; (ii) a system error has occurred; or (iii) a mechanical interference has occurred,
    wherein the electronics are configured to determine that system error has occurred if at least one of (a) the load cells data is out of a load cell data limit range and the accelerometer data is within an accelerometer data limit range and (b) the load cell data is out of the load cell data limit range, the accelerometer data is out of the accelerometer data limit range and the load cell data is dissimilar to the accelerometer data.

15. The dialysis system of claim 14, wherein the electronics are configured to determine that the system is operating properly if at least the load cell data is within a load cell data limit range.

16. The dialysis system of claim 14, wherein the electronics are configured to determine that mechanical interference has occurred if at least the accelerometer data is out of an accelerometer data limit range.

17. The dialysis system of claim 14, wherein the electronics are configured to determine that mechanical interference has occurred if the load cell data is out of a load cell data limit range, the accelerometer data is out of an accelerometer data limit range and the load cell data is similar to the accelerometer data.

18. The dialysis system of claim 14, wherein at least one of the load cell and accelerometer is configured to generate corresponding data continuously, intermittently or upon command.

19. The dialysis system of claim 14, wherein the accelerometer is configured and positioned such that it does not weigh dialysate located within the at least one container.

20. A dialysis system comprising:
an enclosure;
a dialysate pump carried by the enclosure and arranged to pump dialysate to a patient or dialyzer;
at least one container connected fluidly to the dialysate pump;
a load cell positioned to weigh dialysate located within the container;
an accelerometer positioned and arranged to detect a force imparted on at least one of the enclosure and the container; and
electronics configured to receive load cell data from the load cell and accelerometer data from the accelerometer and process the load cell and accelerometer data so as to compensate for errors in the load cell data using the accelerometer data,
wherein the electronics are configured to determine that mechanical interference has occurred if the load cell data is out of a load cell data limit range, the accelerometer data is out of an accelerometer data limit range and the load cell data is similar to the accelerometer data.

21. The dialysis system of claim 20, wherein the electronics are further configured to use the load cell and accelerometer data determine if: (i) the dialysis system is operating properly; (ii) a system error has occurred; or (iii) a mechanical interference has occurred.

22. The dialysis system of claim 20, wherein the accelerometer is a multidimensional accelerometer and the electronics are configured to compensate the load cell data based on at least one force detected by the accelerometer having a non-vertical vector direction.

23. A dialysis system comprising:
an enclosure;
a dialysate pump carried by the enclosure and arranged to pump dialysate to a patient or dialyzer;
at least one container connected fluidly to the dialysate pump;
a load cell positioned to weigh dialysate located within the at least one container;
an accelerometer positioned and arranged to detect a force imparted on at least one of the enclosure and the container; and
electronics configured to receive a first signal from the load cell and a second signal from the accelerometer and process the first and second signals so as to determine if an abnormality sensed by the load cell is a system error or a mechanical interference,
wherein the electronics are configured such that if the second signal yields an abnormal accelerometer condition, and the load cell abnormality and the abnormal accelerometer condition are consistent with a system failure, the load cell abnormality is categorized as a system error.

* * * * *